(12) United States Patent
Chaudhary

(10) Patent No.: US 9,890,266 B2
(45) Date of Patent: Feb. 13, 2018

(54) DIALKYL 2, 5-FURANDICARBOXYLATE PLASTICIZERS AND PLASTICIZED POLYMERIC COMPOSITIONS

(71) Applicant: Dow Global Technologies LLC, Midland, MI (US)

(72) Inventor: Bharat I. Chaudhary, Princeton, NJ (US)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 14/783,922

(22) PCT Filed: May 12, 2014

(86) PCT No.: PCT/US2014/037623
§ 371 (c)(1),
(2) Date: Oct. 12, 2015

(87) PCT Pub. No.: WO2014/193634
PCT Pub. Date: Dec. 4, 2014

(65) Prior Publication Data
US 2016/0145415 A1     May 26, 2016

Related U.S. Application Data

(60) Provisional application No. 61/828,220, filed on May 29, 2013.

(51) Int. Cl.
C08K 5/1535     (2006.01)
C07D 307/68    (2006.01)
H01B 3/44       (2006.01)

(52) U.S. Cl.
CPC .......... *C08K 5/1535* (2013.01); *C07D 307/68* (2013.01); *H01B 3/443* (2013.01)

(58) Field of Classification Search
CPC ............................ C08K 5/1535; C07D 307/68
USPC ........................................................ 549/485
See application file for complete search history.

(56) References Cited

U.S. PATENT DOCUMENTS

| 5,246,783 | A   | 9/1993  | Spenadel et al. |
| 6,496,629 | B2  | 12/2002 | Ma et al.       |
| 6,714,707 | B2  | 3/2004  | Rossi et al.    |
| 9,133,321 | B2* | 9/2015  | Becker ................ C07D 307/68 |
| 9,145,379 | B2* | 9/2015  | Grabeta .............. C07D 307/68 |
| 9,169,228 | B2* | 10/2015 | Grass ................. C07D 307/68 |
| 9,175,148 | B2* | 11/2015 | Becker ................ C07D 307/68 |
| 2012/0202725 | A1 | 8/2012  | Grass et al.   |
| 2012/0220507 | A1 | 8/2012  | Grass et al.   |
| 2013/0338276 | A1 | 12/2013 | Becker et al.  |
| 2015/0203657 | A1 | 7/2015  | Gredegard et al. |

FOREIGN PATENT DOCUMENTS

| WO | WO 2011023491 A1 * | 3/2011  | ........... C07D 307/68 |
| WO | WO 2011023590 A1 * | 3/2011  | ........... C07D 307/68 |
| WO | WO 2012113607 A1 * | 8/2012  | ........... C07D 307/68 |
| WO | WO 2012113608 A1 * | 8/2012  | ........... C07D 307/68 |
| WO | 2013/055961 A1     | 4/2013  |                         |
| WO | 2013/184661 A1     | 12/2013 |                         |
| WO | WO 2013184661 A1 * | 12/2013 | ........... C08K 5/1535 |
| WO | 2014/193634 A1     | 12/2014 |                         |

OTHER PUBLICATIONS

Hartman (Nitrous Oxide Performance Handbook. Motorbooks Workshop. 2009, p. 16).*
ExxonMobil (Exxal 10 Isodecyl Alcohol. ExxonMobil. 2013, 1 page).*
Wypych (Epoxidized Soybean Oil (Drapex 39). Databook of Plasticizers, 2nd Edition., 2017, 4 pages).*
Sanderson, R.D. et al, Synthesis and Eval of Dialkyl Furan-2,5-Dicarboxylates as Plasticizers for PVC, J App Poly Sci, 1994, vol. 53, 1785-1793.
Sanderson, R.D, et al,Synthesis and Eval of Some Functionalized Difuran Diesters J App Pol Sci, 1995, vol. 57, 727-738.
PCT/US2014/037623, International Search Report and Written Opinion. dated Aug. 14, 2014.
PCT/US2014/037623, International Preliminary Report on Patentability. dated May 29, 2013.

* cited by examiner

*Primary Examiner* — Brieann R Johnston
(74) *Attorney, Agent, or Firm* — Husch Blackwell LLP

(57) ABSTRACT

Plasticizers comprising a dialkyl 2,5-furandicarboxylate and plasticized polymeric compositions comprising such plasticizers. Such plasticized polymeric compositions can be employed in forming various articles of manufacture, such as coated conductors.

13 Claims, No Drawings

DIALKYL 2, 5-FURANDICARBOXYLATE PLASTICIZERS AND PLASTICIZED POLYMERIC COMPOSITIONS

REFERENCE TO RELATED APPLICATIONS

The present application claims the benefit of U.S. Provisional Application No. 61/828,220, filed on May 29, 2013.

FIELD

Various embodiments of the present invention relate to plasticizers comprising one or more dialkyl 2,5-furandicarboxylates and plasticized polymeric compositions prepared therewith.

INTRODUCTION

Plasticizers are compounds or mixtures of compounds that are added to polymer resins that can lower the modulus and tensile strength, and increase flexibility, elongation, impact strength, and tear strength of the resin (typically a thermoplastic polymer) to which they are added. A plasticizer may also lower the glass transition temperature of the polymer resin, which enhances processability of the polymer resin.

Phthalic acid diesters (also known as "phthalates") are commonly used as plasticizers in many flexible polymer products, such as polymer products formed from polyvinyl chloride ("PVC") and other vinyl polymers. Examples of phthalate plasticizers include diisononyl phthalate, diallyl phthalate, di-2-ethylhexyl-phthalate, dioctyl phthalate, and diisodecyl phthalate.

Phthalate plasticizers have recently come under intense scrutiny by public interest groups concerned about the negative environmental impact of phthalates and potential adverse health effects in humans exposed to phthalates. Accordingly, suitable replacements for phthalate plasticizers are desired.

SUMMARY

One embodiment is a plasticized polymeric composition, comprising:
a polymer; and
a plasticizer comprising a dialkyl 2,5-furandicarboxylate having the structure:

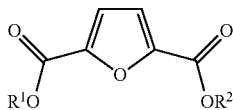

wherein $R^1$ and $R^2$ are independently selected alkyl groups,
wherein at least one of $R^1$ and $R^2$ is selected from alkyl groups having from 10 to 13 carbon atoms,
wherein said plasticizer is a liquid at 22° C. and 1 atmosphere of pressure.

DETAILED DESCRIPTION

Various embodiments of the present invention concern plasticizers comprising a dialkyl 2,5-furandicarboxylate. These plasticizers can also optionally include an epoxidized natural oil, an epoxidized fatty acid alkyl ester, or both. Such plasticizers can be combined with a polymeric resin to form plasticized polymeric compositions, which can in turn be employed in various articles of manufacture.

Plasticizer

The present disclosure provides a plasticizer comprising a dialkyl 2,5-furandicarboxylate. In an embodiment, the plasticizer is phthalate-free, or is otherwise devoid or substantially devoid of phthalates. Additionally, such plasticizers can be devoid or substantially devoid of trimellitates. As used herein, "substantially devoid" means a concentration of 10 parts per million by weight or less.

The plasticizers provided for herein can comprise a dialkyl 2,5-furandicarboxylate having the structure:

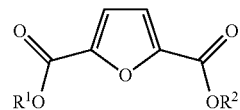

where $R^1$ and $R^2$ are independent alkyl groups. As used herein, the term "alkyl" denotes a univalent group formed by removing a hydrogen atom from a hydrocarbon. In one or more embodiments, $R^1$ and $R^2$ can be the same alkyl group. In an embodiment, $R^1$ and $R^2$ can independently be any saturated or unsaturated, straight-chain, branched, or cyclic $C_1$ to $C_{20}$ (i.e., having from 1 to 20 carbon atoms), $C_1$ to $C_{12}$, or $C_8$ to $C_{13}$ alkyl group. In various embodiments, $R^1$ and $R^2$ are each saturated, straight-chain or branched $C_8$ to $C_{13}$ alkyl group. In one or more embodiments, $R^1$ and $R^2$ are selected from branched $C_{10}$ to $C_{13}$ alkyl groups. In various embodiments, $R^1$ and $R^2$ are the same alkyl group. Specific examples of alkyl groups suitable for use as $R^1$ and $R^2$ include, but are not limited to, 2-ethylhexyl, octyl, nonyl, decyl, dodecyl, isotridecyl, and tridecyl. In an embodiment, each of $R^1$ and $R^2$ is an isotridecyl alkyl group. In other embodiments, each of $R^1$ and $R^2$ is an n-decyl group.

In various embodiments, the plasticizer can comprise mixtures of dialkyl 2,5-furandicarboxylates wherein the alkyl groups $R^1$ and $R^2$ comprise two or more different structures. For example, in various embodiments, the plasticizer can comprise a mixture of dialkyl 2,5-furandicarboxylates including didecyl 2,5-furandicarboxylate, dioctyl 2,5-furandicarboxylate, and bis(2-ethylhexyl) 2,5-furandicarboxylate. Additionally, the plasticizer can comprise a mixture of dialkyl 2,5-furandicarboxylates having alkyl groups selected from 2-ethylhexyl, octyl, and decyl groups. It should be understood that such mixtures may contain dialkyl 2,5-furandicarboxylates wherein $R^1$ and $R^2$ are the same or different. For example, such a mixture could include the following molecules: (1) didecyl 2,5-furandicarboxylate, (2) dioctyl 2,5-furandicarboxylate, (3) bis(2-ethylhexyl) 2,5-furandicarboxylate, (4) decyl octyl 2,5-furandicarobxylate, (5) decyl 2-ethylhexyl 2,5-furandicarboxylate, and (6) octyl 2-ethylhexyl 2,5-furandicarboxylate. In other words, in various embodiments, $R^1$ and $R^2$ in the above structure can be independently selected from a combination of 2-ethylhexyl, octyl, and decyl alkyl groups. In such embodiments, the mixture of dialkyl 2,5-furandicarboxylates can comprise dialkyl 2,5-furandicarboxylates having alkyl groups of at least 10 carbon atoms in an amount of at least 10 mole percent ("mol %"), at least 15 mol %, at least 20 mol %, or at least 25 mol % based on the total amount of dialkyl 2,5-furandicarboxylates in the plasticizer. In such embodiments, the concentration of the dialkyl 2,5-furandicarboxylate having alkyl groups of at least 10 carbon atoms can be up to 90 mol %, up to 80 mol %, up to 70 mol %, up to 60 mol %, up to 50 mol %, up to 40 mol %, or up to 30 mol %, based on the total amount of dialkyl 2,5-furandicarboxylates in the plasticizer. In these embodiments, the alkyl groups of the dialkyl 2,5-furandicarboxylate can have a number of carbon atoms ranging from 10 to 13.

The plasticizers suitable for use herein are liquid at 22° C. and 1 atmosphere of pressure ("atm"). Accordingly, in various embodiments, the dialkyl 2,5-furandicarboxylate or mixtures of two or more dialkyl 2,5-furandicarboxylates can be liquid at 22° C. and 1 atm.

Dialkyl 2,5-furandicarboxylates suitable for use herein can be prepared using any known or hereafter discovered esterification methods in the art. Specifically, dialkyl 2,5-furandicarboxylates can be prepared by an esterification reaction between 2,5-furandicarboxylic acid and a suitable alcohol or combination of alcohols containing the desired alkyl moiety or moieties. For instance, if diisotridecyl 2,5-furandicarboxylate is the desired product, one can select isotridecyl alcohol and 2,5-furandicarboxylic acid as the reagents in appropriate amounts (e.g., at least a 2:1 molar ratio of alcohol-to-dicarboxylic acid) for the esterification reaction. Alternatively, as would be known to those of ordinary skill in the art, transesterification could be employed using a 2,5-furandicarboxylate and a suitable alcohol as starting reagents. Typical esterification conditions could include performing the reaction at elevated temperature (e.g., 170° C.), under mechanical agitation, and in the presence of a catalyst (e.g., an acid catalyst, such as sulfuric acid). Following esterification, water and excess alcohol can be removed via conventional methods.

In various embodiments, the present plasticizer can include a second plasticizer component selected from the group consisting of an epoxidized natural oil ("eNO"), an epoxidized fatty acid alkyl ester ("eFAAE"), and combinations thereof. A "natural oil," as used herein, is an oil composed of fatty acid triglycerides and derived from a microbe (algae, bacteria), a plant/vegetable, and/or a seed. In an embodiment, natural oils include genetically-modified natural oils. The term "natural oil" excludes petroleum-derived oil. Non-limiting examples of suitable natural oils include beef tallow oil, canola oil, castor oil, corn oil, fish oil, linseed oil, palm oil, rapeseed oil, safflower oil, soybean oil, sunflower oil, tall oil, tung oil, and any combination thereof.

The term "epoxidized natural oil," as used herein, is a natural oil wherein at least one fatty acid moiety contains at least one epoxide group. Epoxidation may be performed via conventional methods, typically by way of reaction of a natural oil with a peroxide, a percarboxylic acid, and/or other peroxy compounds, often in the presence of an acid or base catalyst.

Non-limiting examples of suitable eNOs include epoxidized algae oil, epoxidized beef tallow oil, epoxidized canola oil, epoxidized castor oil, epoxidized corn oil, epoxidized fish oil, epoxidized linseed oil, epoxidized palm oil, epoxidized rapeseed oil, epoxidized safflower oil, epoxidized soybean oil, epoxidized sunflower oil, epoxidized tall oil, epoxidized tung oil, and any combination thereof.

In an embodiment, the epoxidized natural oil is an epoxidized soybean oil ("eSO").

Examples of suitable commercially available epoxidized natural oils include PLAS-CHEK™ 775 epoxidized soybean oil, available from Ferro Corp., Mayfield Heights, Ohio, USA; VIKOFLEX™ 7170 epoxidized soybean oil, and VIKOFLEX™ 7190 epoxidized linseed oil, both available from Arkema Inc., Philadelphia, Pa., USA.

As noted above, the plasticizer can optionally contain, as part or all of a second plasticizer component, an epoxidized fatty acid alkyl ester ("eFAAE"), such as epoxidized fatty acid methyl ester. Non-limiting examples of commercially available eFAAEs include VIKOFLEX™ 7010, VIKOFLEX™ 7040, VIKOFLEX™ 7080, VIKOFLEX™ 9010, VIKOFLEX™ 9040, and VIKOFLEX™ 9080 (products of Arkema Inc., Philadelphia, Pa., USA).

In an embodiment, when a second plasticizer component is employed, the plasticizer can contain the dialkyl 2,5-furandicarboxylate in an amount ranging from 10 to 90 weight percent ("wt %"), from 30 to 70 wt %, or about 50 wt % based on the entire plasticizer weight. In a further embodiment, the plasticizer can contain the second plasticizer component (i.e., eNO and/or eFAAE) in an amount ranging from 10 to 90 wt %, from 30 to 70 wt %, or about 50 wt % based on the entire plasticizer weight. Thus, in various embodiments, the dialkyl 2,5-furandicarobxylate and the second plasticizer component can be present in a weight ratio ranging from 9:1 to 1:9, from 7:3 to 3:7, or about 1:1 dialkyl 2,5-furandicarboxylate-to-secondary plasticizer component. In one or more embodiments, the plasticizer consists of or consists essentially of dialkyl 2,5-furandicarboxylate with eNO and/or eFAAE.

Polymeric Composition

The present disclosure provides a polymeric composition comprising a polymer and the above-described plasticizer.

Non-limiting examples of suitable polymers include polysulfides, polyurethanes, acrylics, epichlorohydrins, nitrile rubber, chlorosulfonated polyethylene, chlorinated polyethylene, polychloroprene, styrene butadiene rubber, natural rubber, synthetic rubber, ethylene-propylene-diene monomer rubber, propylene-based polymers, ethylene-based polymers, and vinyl chloride resins. The term "propylene-based polymer" denotes a polymer comprising a majority weight percent polymerized propylene monomer (based on the total amount of polymerizable monomers) and optionally at least one polymerized comonomer. The term "ethylene-based polymer" denotes a polymer comprising a majority weight percent polymerized ethylene monomer (based on the total weight of polymerizable monomers) and optionally at least one polymerized comonomer.

The term "vinyl chloride resin" denotes a vinyl chloride polymer, such as polyvinyl chloride ("PVC"), or a vinyl chloride copolymer, such as vinyl chloride/vinyl acetate copolymer, vinyl chloride/vinylidene chloride copolymer, vinyl chloride/ethylene copolymer, or a copolymer prepared by grafting vinyl chloride onto ethylene/vinyl acetate copolymer. The vinyl chloride resin can also include a polymer blend of the above-mentioned vinyl chloride polymer or vinyl chloride copolymer with other miscible or compatible polymers including, but not limited to, chlorinated polyethylene, thermoplastic polyurethane, olefin polymers such as a methacryl polymer, or acrylonitrile-butadiene-styrene polymer.

In an embodiment, the vinyl chloride resin is PVC.

In an embodiment, the polymeric composition comprises the polymer in an amount ranging from 20 to 90 wt %, from 30 to 85 wt %, from 40 to 80 wt %, or from 50 to 65 wt %, based on the entire polymeric composition weight. In various embodiments, the polymeric composition comprises the above-described plasticizer in an amount ranging from 10 to 80 wt %, from 15 to 70 wt %, from 20 to 60 wt %, or from 25 to 35 wt %, based on the entire polymeric composition weight.

In various embodiments, the polymeric composition can have a Shore D hardness of less than 43, or less than 41, as determined by ASTM D2240. In such embodiments, the polymeric composition can have a minimum Shore D hardness of 25. In one or more embodiments, the polymeric composition can have a Shore A hardness of less than 96, or less than 94, as determined by ASTM D2240. In such embodiments, the polymeric composition can have a minimum Shore A hardness of 81. Shore hardness (both A and D) is determined on polymeric compositions having a plasticizer loading of 52 parts per hundred resin ("phr") based on 100 parts by weight of the polymer.

In various embodiments, the polymeric composition has a tensile elongation retention ("TER") of at least 30%, at least 40%, at least 50%, at least 60%, or at least 70% after heat aging at 100° C., 113° C., and/or 136° C. for 168 hours, as determined by ASTM D638. Heat-aging of polymeric compositions is performed according to the procedure described below in the following Test Methods section. TER can be determined on polymeric compositions having a plasticizer loading of 52 phr.

In various embodiments, the polymeric composition has a tensile strength retention ("TSR") of at least 50%, at least 60%, at least 70%, at least 80%, at least 90%, or at least 100% after heat aging at 100° C., 113° C., and/or 136° C. for 168 hours, as determined by ASTM D638. TSR can be determined on polymeric compositions having a plasticizer loading of 52 phr.

In various embodiments, the polymeric composition has a weight retention of at least 50%, at least 55%, at least 60%, or at least 65% after heat aging at 100° C., 113° C., and/or 136° C. for 168 hours. Weight retention can be determined on polymeric compositions having a plasticizer loading of 52 phr.

Additives

The polymeric composition may include one or more of the following optional additives: a filler, a flame retardant, a heat stabilizer, an anti-drip agent, a colorant, a lubricant, a low-molecular-weight polyethylene, a hindered amine light stabilizer, a UV light absorber, a curing agent, a booster, a retardant, a processing aid, a coupling agent, an antistatic agent, a nucleating agent, a slip agent, a viscosity control agent, a tackifier, an anti-blocking agent, a surfactant, an extender oil, an acid scavenger, a metal deactivator, and any combination thereof.

In an embodiment, the polymeric composition comprises a heat stabilizer. Non-limiting examples of suitable heat stabilizers include lead-free metal soaps, lead stabilizers, organic heat stabilizers, epoxides, salts of monocarboxylic acids, phenolic antioxidants, organic phosphites, and/or betadiketones. In an embodiment, the heat stabilizer employed is a lead-free mixed metal soap. The term "metal soap" denotes a salt of an acid with a metal. Metal soaps suitable for use include zinc salts of fatty acids (e.g., zinc stearate), calcium salts of fatty acids, barium salts of fatty acids, magnesium salts of fatty acids, tin salts of fatty acids, and mixtures of two or more thereof. Heat stabilizers can be present in the polymeric composition in an amount ranging from 0.2 to 10 wt %, from 0.4 to 7 wt %, or from 0.6 to 5 wt %, based on the entire polymeric composition weight.

In an embodiment, the polymeric composition includes PVC, the present plasticizer, a filler (e.g., calcium carbonate, clays, silica, and any combination thereof), one or more metal soap stabilizers, a phenolic or other antioxidant, and a processing aid.

Coated Conductor

The present disclosure provides a coated conductor. The coated conductor includes a conductor and a coating on the conductor or on an interceding layer covering the conductor, the coating at least partially being formed from the polymeric composition described above.

A "conductor," as used herein, is one or more wire(s) or fiber(s) for conducting heat, light, and/or electricity. The conductor may be a single-wire/fiber or a multi-wire/fiber and may be in strand form or in tubular form. "Wire" means a single strand of conductive metal or a single strand of optical fiber. Non-limiting examples of suitable conductors include metals such as silver, gold, copper, carbon, and aluminum. The conductor may also be optical fiber made from either glass or plastic.

The coated conductor may be flexible, semi-rigid, or rigid. The coating (also referred to as a "jacket," "sheath," or "insulation") can be located either directly on the conductor or on another layer that surrounds the conductor.

In an embodiment, the coated conductor is a cable. "Cable" and "power cable" mean at least one wire or optical fiber within a sheath. Typically, a cable is two or more wires or optical fibers bound together, typically in a common insulation covering and/or protective jacket. The individual wires or fibers inside the sheath may be bare, covered or insulated. Combination cables may contain both electrical wires and optical fibers. The cable can be designed for low, medium, and/or high voltage applications. Typical cable designs are illustrated in U.S. Pat. Nos. 5,246,783, 6,496,629 and 6,714,707.

In an embodiment, the cable is a 60° C., 75° C., 80° C., 90° C., or 105° C.-rated cable according to Underwriters Laboratories ("UL") standards 83 and 1581.

Test Methods

Shore Hardness

Determine Shore (A and D) hardness according to ASTM D2240 using molded specimens of 250-mil (6.35 mm) thickness.

Tensile Properties

Determine tensile strength, tensile elongation, and secant modulus for both unaged and heat-aged samples according to ASTM D638 at a displacement rate of 2 inches per minute on Type IV dog-bone-shaped specimens that are cut from 30-mil (0.762 mm) thick molded plaques.

Volume Resistivity

Determine volume resistivity (ohm·cm at 23° C.) with 500 volts direct current in accordance with ASTM D257. Employ 3.5-inch (8.89 cm) diameter specimens cut from 40-mil (1.016 mm) thick molded plaques and a Hewlett Packard 16008A Resistivity Cell connected to a Hewlett Packard 4329A High Resistance Meter.

Dynamic Storage Modulus (E')

Determine dynamic storage modulus (E') by dynamic mechanical analysis ("DMA") using a TA Instrument Q800 rheometer having single cantilever fixture. The specimen is in the form of a rectangular solid (35 mm long×13 mm wide×40 mil thick) and tested in bending mode. Each rectangular solid sample is clamped at both ends, such that the length between the clamped positions is 17.5 mm, and bent at one end along its length during the test. The movable end of the sample is oscillated (up and down) at an amplitude of 25 micrometer while the other end is held steady. The temperature is varied from −100° C. to +100° C. at a ramp rate of 5° C./minute, and the frequency of oscillation is held constant at 6.283 rad/s (1 Hz). The storage and loss modulus of the sample, as well as the tan delta, are measured as a function of the temperature. The mechanical modulii obtained through this deformation mode are Young's modulii (E', E"). Dynamic storage modulus (E') at −20° C. is used as a measure of low-temperature flexibility. The storage and loss modulus of viscoelastic materials are measures of the stored energy (representing the elastic portion) and the energy dissipated as heat (representing the viscous portion).

Loop Spew and Plasticizer Compatibility

Measure loop spew in accordance with ASTM D3291 on specimens of 75-mil (1.905 mm) thickness. Plasticizer compatibility in the polymeric composition is also assessed by visual inspection of molded or extruded specimens aged at elevated temperatures (e.g., 100° C. or 113° C. or 136° C.) for defined lengths of time (e.g., 7 days). The extruded specimens may be in the form of a wire (i.e., insulation extruded over conductor).

Weight Retention

Measure weight retained, expressed as a percentage, after various days at elevated temperatures on specimens of 1.25 inches (3.715 cm) in diameter that are cut from 30-mil (0.762 mm) thick molded plaques.

Heat Aging

Heat aging for tensile and weight retention specimens (of geometries described above) is conducted using a Type II ASTM D5423-93 Testing Mechanical Convection Oven.

Reagents

In the Examples detailed below, the following reagents are employed:

Furan 2,5-dicarboxylic acid, 2-ethylhexanol, 1-dodecanol, 1-octanol, 1-decanol, sulfuric acid, and magnesium silicate are all available from Sigma-Aldrich, St. Louis, Mo., USA.

Isotridecyl alcohol is available from BOC Sciences, Shirley, N.Y., USA.

The polyvinyl chloride ("PVC") employed is OXYVINYLS™ 240F, available from Occidental Chemical Corporation, Dallas, Tex., USA.

The filler employed is SATINTONE™ SP-33 Clay, available from BASF Corporation, Florham Park, N.J., USA.

The heat stabilizer is a calcium/zinc metal soap sold under the name BAEROPAN™ MC 90249 KA, available from Baerlocher USA, Dover, Ohio, USA.

The flame retardant is antimony trioxide sold under the name MICROFINE™ A09, available from Chemtura Corp., Middlebury, Conn., USA.

The antioxidant is IRGANOX™ 1076, available from BASF Corporation, Florham Park, N.J., USA.

The bis(2-ethylhexyl) phthalate ("DEHP") is available from Alfa Aesar, Ward Hill, Mass., USA.

The diisodecyl phthalate ("DIDP") is available from TCI Tokyo Kasei, Tokyo, Japan.

The trioctyl trimellitate ("TO™") is available from Sigma-Aldrich, St. Louis, Mo., USA.

The epoxidized soybean oil ("eSO") is sold under the trade name PLAS-CHEK™ 775, and is available from Ferro Corp., Mayfield Heights, Ohio, USA.

The epoxidized fatty acid methyl ester ("eFAME") is sold under the trade name VIKOFLEX™ 7010, and is available from Arkema, Inc., King of Prussia, Pa., USA.

EXAMPLES

Example 1—Preparation of Dialkyl 2,5-Furandicarboxylates

Prepare six different dialkyl 2,5-furandicarboxylates according to the following procedures. Note that dialkyl 2,5-furandicarboxylates that are solid at room temperature are considered unsuitable for use as plasticizers.

Bis(2-ethylhexyl) 2,5-furandicarboxylate

Prepare bis(2-ethylhexyl) 2,5-furandicarboxylate ("2-EH FDC") by weighing 461.44 g of 2-ethylhexanol into a 2000-mL four-neck round-bottom flask. Add a condenser, Dean-Stark trap, thermometer with a thermowatch temperature regulator, an overhead mechanical stirrer, stopper, and $N_2$ inlet. Turn on the stirrer. Add 171.51 g of furan 2,5-dicarboxylic acid to the flask. Wrap insulation around the flask and Dean-Stark trap. Add a few drops of sulfuric acid, and turn the temperature up to 170° C. Start overhead collection and mix the contents of the flask overnight. The following day, confirm completion of reaction by gas chromatography ("GC"). Collect $H_2O$ and 2-ethylhexanol from the Dean-Stark trap and turn off the heat. The sample is a very clear, bright-orange color. To remove the excess 2-ethylhexanol, evaporate the sample using a rotary evaporator (secured with a pump) with the water bath set at 85° C. If GC confirms an excess of 2-ethylhexanol is still present, subject the sample to wiped film evaporation ("WFE") using a jacket temperature of 105° C., a cold finger temperature of 15° C., a stir speed of 246 rpm, a pressure of 100 millitorr ("mTorr") and a flow rate of 1.5 mL/minute. Discard the overhead. The resulting material is a liquid at room temperature.

Didodecyl 2,5-furandicarboxylate

Prepare didodecyl 2,5-furandicarboxylate ("C12 FDC") by weighing 203.38 g of furan 2,5-dicarboxylic acid into a 2000-mL four-neck round-bottom flask. Add a condenser, Dean-Stark trap, thermometer with a thermowatch temperature regulator, an overhead mechanical stirrer, stopper, and $N_2$ inlet. Turn on the stirrer. Wrap insulation around the flask and Dean-Stark trap. Add 723.9 g of 1-dodecanol to the flask, and turn the temperature up to 180° C. Add 5 drops of sulfuric acid. After 5 hours, if no collection is present in the Dean-Stark trap, increase the heat to 190° C. Start overhead collection of water and mix the contents of the flask overnight. The following day, add an additional 80 mL of 1-dodecanol and 2 additional drops of sulfuric acid. Turn the heat up to 195° C. Following confirmation via GC that the reaction is complete, stop the reaction. As the reaction mixture cools, solids precipitate out of the reaction medium. The resulting didodecyl 2,5-furandicarboxylate is a solid at room temperature.

Mixed (75/25%) 2-EH and C12 FDC

Prepare a mixed 2,5-furandicarboxylate having 2-ethylhexyl and dodecyl alkyl substituents by first weighing 78.33 g of furan 2,5-dicarboxylic acid into a 1000-mL four-neck round-bottom flask. Add a condenser, Dean-Stark trap, thermometer with a thermowatch temperature regulator, an overhead mechanical stirrer, stopper, and $N_2$ inlet. Wrap insulation around the flask and Dean-Stark trap. Turn on the stirrer. Add 197.39 g of 2-ethylhexanol and 95.12 g of 1-dodecanol to the flask. Add 5 drops of sulfuric acid and turn the temperature up to 180° C. Start overhead collection of water and mix the contents of the flask overnight. The following day, confirm completion of reaction by GC. Collect $H_2O$ from the Dean-Stark trap and turn off the heat. The sample solidifies as it cools, becoming a solid at room temperature.

Mixed (50/50%) 2-EH and C12 FDC

Prepare a mixed 2,5-furandicarboxylate having 2-ethylhexyl and dodecyl alkyl substituents by first weighing 80.16 g of furan 2,5-dicarboxylic acid into a 1000-mL four-neck round-bottom flask. Add a condenser, Dean-Stark trap, thermometer with a thermowatch temperature regulator, an overhead mechanical stirrer, stopper, and $N_2$ inlet. Wrap insulation around the flask and Dean-Stark trap. Turn on the stirrer. Add 133.1 g of 2-ethylhexanol and 187.01 g of 1-dodecanol to the flask. Add 5 drops of sulfuric acid and turn the temperature up to 180° C. Start overhead collection of water and mix the contents of the flask overnight. The following day, confirm completion of reaction by GC.

Collect H₂O from the Dean-Stark trap and turn off the heat. The sample solidifies as it cools, becoming a solid at room temperature.

Mixed (50/25/25%) 2-EH, C8, and C10 FDC

Prepare a mixed 2,5-furandicarboxylate having 2-ethylhexyl, octyl ("C8"), and decyl ("C10") alkyl substituents (collectively, "2-EH/C8/C10 FDC") by first weighing 79.25 g of furan 2,5-dicarboxylic acid into a 1000-mL four-neck round-bottom flask. Add a condenser, Dean-Stark trap, thermometer with a thermowatch temperature regulator, an overhead mechanical stirrer, stopper, and N₂ inlet. Wrap insulation around the flask and Dean-Stark trap. Turn on the stirrer. Add 161.75 g of 2-ethylhexanol, 84.59 g of 1-octanol, and 102.35 g of 1-decanol to the flask. Add 5 drops of sulfuric acid and turn the temperature up to 180° C. Start overhead collection of water and mix the contents of the flask overnight. The following day, add 2 additional drops of sulfuric acid and allow reaction to proceed. Upon confirming completion of reaction by GC, collect H₂O from the Dean-Stark trap and turn off the heat. The sample is a clear, dark yellow color.

Subject the sample to WFE using a jacket temperature of 160° C., a cold finger temperature of 10° C., a stir speed of 459 rpm, a pressure of 350 mTorr, and a flow rate of 2.0 mL/minute. Discard the overheads. If the resulting sample is still dark in color, subject the sample to WFE again using a jacket temperature of 200° C., a cold finger temperature of 25° C., a stir speed of 372 rpm, a pressure of 180 mTorr, and a flow rate of 3.5 mL/minute; collect the overheads, and discard the bottoms.

To the above sample, of which 133.46 g are collected, apply a 1% magnesium silicate treatment by placing the sample in a 500-mL three-neck round-bottom flask. Add a condenser, N₂ inlet, thermometer with a thermowatch temperature regulator, and an overhead mechanical stirrer. Turn on the stirrer. Add 1.32 g of magnesium silicate. Turn the heat up to 70° C. Once the sample reaches 70° C., allow it to mix for 1 hour. Thereafter, turn off the heat, and, once the sample reaches room temperature, filter the sample using a 90-mm microfiltration unit with filter paper having a 1-micrometer ("μm") pore size. As the sample is being filtered, the color goes from a clear, dark-yellow product to a clear, light-yellow product. 123.23 g are collected. The resulting material is a liquid at room temperature.

Diisotridecyl 2,5-furandicarboxylate

Prepare a diisotridecyl 2,5-furandicarboxylate ("DITD FDC") by first weighing 61.09 g of furan 2,5-dicarboxylic acid into a 1000-mL four-neck round-bottom flask. Add a condenser, Dean-Stark trap, thermometer with a thermowatch temperature regulator, an overhead mechanical stirrer, stopper, and N₂ inlet. Wrap insulation around the flask and Dean-Stark trap. Turn on the stirrer. Add 299.66 g isotridecyl alcohol and turn the temperature up to 180° C. Add 6 drops of sulfuric acid. Start overhead collection of water and mix the contents of the flask overnight. The following day, add 2-3 additional drops of sulfuric acid and allow the reaction to continue while stirring overnight. On the third day, confirm completion of reaction by GC. Collect H₂O from the Dean-Stark trap and turn off the heat. The sample is a clear, dark orange color.

Subject the sample to WFE using a jacket temperature of 140° C., a cold finger temperature of 20° C., a stir speed of 431 rpm, a pressure of 100 mTorr, and a flow rate of 2.0 mL/minute. Discard the overheads. If the resulting sample is still dark in color, subject the sample to WFE again using a jacket temperature of 210° C., a cold finger temperature of 20° C., a stir sped of 459 rpm, a pressure of 160 mTorr, and a flow rate of 2.0 mL/minute; collect the overheads, and discard the bottoms.

To the above sample, of which 162.64 g are collected, apply a 2% magnesium silicate treatment by placing the sample in a 500-mL three-neck round-bottom flask. Add a condenser, N₂ inlet, thermometer with a thermowatch temperature regulator, and an overhead mechanical stirrer. Turn on the stirrer. Add 3 g of magnesium silicate. Turn the heat up to 70° C. Once the sample reaches 70° C., allow it to mix for 1 hour. Thereafter, turn off the heat, and, once the sample reaches room temperature, filter the sample using a 90-mm microfiltration unit with filter paper having a 1 μm pore size. As the sample is being filtered, the color goes from a clear, light-orange product to a clear, yellow product. 140 mL are collected. The resulting diisotridecyl 2,5-furandicarboxylate is a liquid at room temperature.

Example 2—PVC Plasticized with Phthalate or Trimellitate (Comparative)

Prepare three comparative plasticized PVC samples (CS1-CS3) according to the formulations provided in Table 1, below.

TABLE 1

| CS1-CS3 Sample Compositions | | | |
|---|---|---|---|
| | CS1 | CS2 | CS3 |
| PVC (wt %) | 57.3 | 57.3 | 57.3 |
| Filler (wt %) | 6.4 | 6.4 | 6.4 |
| Heat Stabilizer (wt %) | 3.0 | 3.0 | 3.0 |
| Flame Retardant (wt %) | 3.0 | 3.0 | 3.0 |
| Antioxidant (wt %) | 0.3 | 0.3 | 0.3 |
| DEHP (wt %) | 30.0 | — | — |
| DIDP (wt %) | — | 30.0 | — |
| TOTM (wt %) | — | — | 30.0 |
| Total | 100 | 100 | 100 |
| Plasticizer parts per hundred resin ("phr") | ~52 | ~52 | ~52 |

Prepare the above samples by preheating the plasticizer (or plasticizer mixture) to 60° C. for at least 60 minutes and shake by hand for a few seconds before use. After weighing the individual components, prepare "dry blends" by soaking the plasticizer composition into the PVC powder, and then prepare melt mixtures. Prepare "dry blends" as follows:
(a) Mix all ingredients except plasticizer and filler in a container using spatula.
(b) Warm up a 40 cm³ Brabender mixing bowl with sigma blades at 90° C. and 40 rpm for two minutes.
(c) Add the mixed ingredients from step (a) to the mixing bowl and mix for 60 seconds.
(d) Add the plasticizer to the mixing bowl and mix for 10 minutes or 20 minutes, and record time for complete plasticizer absorption, as determined by visual observation.
(e) Add filler and mix for 60 seconds.
(f) Stop and remove the dry blend.

Thereafter, melt mix the "dry blends" using the Brabender mixing bowl with cam rotors at 40 rpm setting and mixing at 180° C. for 10 minutes from the time of loading.

Compression mold the resulting blend compositions at 180° C. for 5 minutes (2 minutes at approximately 500 psi, followed by 3 minutes at approximately 2,000 psi). Employing the procedures described above, measure the properties of (1) unaged specimens, and (2) specimens aged at elevated temperatures. The heat-aged specimens are also examined visually for evidence of exudate (spew) at the surface. The results are provided in Table 2, below.

TABLE 2

Properties of Samples CS1-CS3

|  | CS1 (DEHP) | CS2 (DIDP) | CS3 (TOTM) |
|---|---|---|---|
| Mixing Time after Plasticizer Absorption and Before Filler Addition (min) | 10 | 10 | 10 |
| Plasticizer absorption time (min) | 4.0 | 3.5 | 5.5 |
| Shore D Hardness | 29.6 ± 1.1 | 33.1 ± 0.5 | 35.5 ± 0.7 |
| Shore A Hardness | 84.3 ± 1.0 | 87.9 ± 0.7 | 90.4 ± 1.0 |
| TS, unaged (psi) | 2631 ± 331 | 3296 ± 51 | 3440 ± 139 |
| TSR after 100° C. aging (%) | 116 ± 10 | 98 ± 4 | 89 ± 3 |
| TSR after 113° C. aging (%) | 276 ± 36 | 92 ± 4 | 88 ± 12 |
| TSR after 136° C. aging (%) | 283 ± 30 | 186 ± 20 | 92 ± 5 |
| TE, unaged (%) | 263 ± 51 | 321 ± 3 | 315 ± 12 |
| TER after 100° C. aging (%) | 10 ± 8 | 98 ± 6 | 95 ± 7 |
| TER after 113° C. aging (%) | 2 ± 0 | 80 ± 9 | 88 ± 17 |
| TER after 136° C. aging (%) | 1 ± 0 | 1 ± 0 | 82 ± 6 |
| WR after 100° C. aging (%) | 83.4 | 97.2 | 100.5 |
| WR after 113° C. aging (%) | 75.0 | 92.0 | 100.1 |
| WR after 136° C. aging (%) | 69.9 | 75.2 | 96.9 |
| E' at −20° C. (MPa) | 2.28E+03 | 2.59E+03 | 2.73E+03 |
| Surface Exudate | None | None | None |
| Loop spew, 48 hrs at 23° C. | None | None | None |
| VR at 23° C. (Ohms cm) | 7.44E+15 | 9.14E+15 | 1.46E+16 |

TS = Tensile strength, ASTM D638
TSR = Tensile strength retention, ASTM D638
TSR 100° C. = Tensile strength retention, (%), specimen aged at 100° C. for 168 hours
TSR 113° C. = Tensile strength retention, (%), specimen aged at 113° C. for 168 hours
TSR 136° C. = Tensile strength retention, (%), specimen aged at 136° C. for 168 hours
TE = Tensile elongation, ASTM D638
TER = Tensile elongation retention, ASTM D638
TER 100° C. = Tensile elongation retention (%), specimen aged at 100° C. for 168 hours
TER 113° C. = Tensile elongation retention (%), specimen aged at 113° C. for 168 hours
TER 136° C. = Tensile elongation retention (%), specimen aged at 136° C. for 168 hours
WR = Weight Retained, specimen aged at 100° C., 113° C., and 136° C. for 168 hours
Surface Exudate = inspected at 1, 3, and 7 days @ temperatures from 100 to 136° C.
VR = Volume Resistivity (ohms · cm)

Example 3—PVC Plasticized with 2-EH FDC, 2-EH/C8/C10 FDC, or DITD FDC

Prepare six plasticized PVC samples according to the formulations provided in Table 3, below, using the procedure described in Example 2, above. Samples prepared with 2-EH FDC are comparative (CS4 and CS5). Samples S1 and S2 are prepared with the mixed 2-EH/C8/C10 FDC plasticizer, and Samples S3 and S4 are prepared with the DITD FDC plasticizer.

TABLE 3

CS4, CS5, and S1-S4 Sample Compositions

|  | CS4 | CS5 | S1 | S2 | S3 | S4 |
|---|---|---|---|---|---|---|
| PVC (wt %) | 57.3 | 57.3 | 57.3 | 57.3 | 57.3 | 57.3 |
| Filler (wt %) | 6.4 | 6.4 | 6.4 | 6.4 | 6.4 | 6.4 |
| Heat Stabilizer (wt %) | 3.0 | 3.0 | 3.0 | 3.0 | 3.0 | 3.0 |
| Flame Retardant (wt %) | 3.0 | 3.0 | 3.0 | 3.0 | 3.0 | 3.0 |
| Antioxidant (wt %) | 0.3 | 0.3 | 0.3 | 0.3 | 0.3 | 0.3 |
| 2-EH FDC (wt %) | 30.0 | 30.0 | — | — | — | — |
| 2-EH/C8/C10 FDC (wt %) | — | — | 30.0 | 30.0 | — | — |
| DITD FDC (wt %) | — | — | — | — | 30.0 | 30.0 |
| Total | 100 | 100 | 100 | 100 | 100 | 100 |
| Plasticizer phr | ~52 | ~52 | ~52 | ~52 | ~52 | ~52 |

Analyze Samples CS4, CS5, and S1-S4 according to the above-described procedures. The results are provided in Table 4, below.

TABLE 4

Properties of Samples CS4, CS5, and S1-S4

|  | CS4 (2-EH FDC) | CS5 (2-EH FDC) | S1 (2-EH/C8/ C10 FDC) | S2 (2-EH/C8/ C10 FDC) | S3 (DITD FDC) | S4 (DITD FDC) |
|---|---|---|---|---|---|---|
| Mixing Time after Plasticizer Absorption and Before Filler Addition (min) | 10 | 20 | 10 | 20 | 20 | 20 |
| Plasticizer absorption time (min) | 3.0 | 4.0 | 3.0 | 4.0 | 20.0 | 18.0 |
| Shore D Hardness | 27.9 ± 0.5 | 28.5 ± 0.7 | 29.3 ± 0.7 | 26.4 ± 0.5 | 37.6 ± 1.5 | 39.6 ± 1.6 |
| Shore A Hardness | 83.8 ± 0.6 | 83.3 ± 1.6 | 84.8 ± 0.6 | 83.9 ± 0.7 | 92.6 ± 0.4 | 93.2 ± 1.0 |
| TS, unaged (psi) | 2757 ± 142 | 2874 ± 94 | 2918 ± 80 | 2714 ± 31 | 3295 ± 193 | 2723 ± 318 |
| TSR after 100° C. aging (%) | 147 ± 19 | 112 ± 18 | 114 ± 6 | 102 ± 3 | 91 ± 33 | 119 ± 16 |
| TSR after 113° C. aging (%) | 202 ± 33 | 198 ± 19 | 111 ± 9 | 106 ± 6 | 102 ± 8 | 96 ± 18 |
| TSR after 136° C. aging (%) | 235 ± 23 | 219 ± 16 | 271 ± 12 | 205 ± 15 | 109 ± 8 | 106 ± 22 |
| TE, unaged (%) | 290 ± 13 | 287 ± 11 | 321 ± 14 | 295 ± 5 | 316 ± 15 | 266 ± 48 |
| TER after 100° C. aging (%) | 4 ± 2 | 21 ± 23 | 94 ± 9 | 96 ± 7 | 83 ± 46 | 118 ± 23 |
| TER after 113° C. aging (%) | 1 ± 0 | 2 ± 0 | 86 ± 3 | 84 ± 2 | 106 ± 9 | 104 ± 28 |
| TER after 136° C. aging (%) | 1 ± 0 | 1 ± 0 | 1 ± 0 | 1 ± 0 | 81 ± 5 | 83 ± 26 |
| WR after 100° C. aging (%) | 86.5 | 87.5 | 95.4 | 96.2 | 100.0 | 99.5 |
| WR after 113° C. aging (%) | 77.6 | 75.2 | 90.5 | 88.6 | 99.4 | 98.3 |
| WR after 136° C. aging (%) | 71.7 | 70.7 | 74.0 | 71.3 | 93.1 | 91.5 |

TABLE 4-continued

Properties of Samples CS4, CS5, and S1-S4

|  | CS4 (2-EH FDC) | CS5 (2-EH FDC) | S1 (2-EH/C8/C10 FDC) | S2 (2-EH/C8/C10 FDC) | S3 (DITD FDC) | S4 (DITD FDC) |
|---|---|---|---|---|---|---|
| E' at −20° C. (MPa) | 2.40E+03 | — | 2.14E+03 | — | 2.37E+03 | — |
| Surface Exudate | None | None | None | None | None | None |
| Loop spew, 48 hrs at 23° C. | None | None | None | Slight | None | None |
| VR at 23° C. (Ohms cm) | 1.41E+15 | — | 9.26E+14 | — | 3.21E+15 | — |

TS = Tensile strength, ASTM D638
TSR = Tensile strength retention, ASTM D638
TSR 100° C. = Tensile strength retention, (%), specimen aged at 100° C. for 168 hours
TSR 113° C. = Tensile strength retention, (%), specimen aged at 113° C. for 168 hours
TSR 136° C. = Tensile strength retention, (%), specimen aged at 136° C. for 168 hours
TE = Tensile elongation, ASTM D638
TER = Tensile elongation retention, ASTM D638
TER 100° C. = Tensile elongation retention (%), specimen aged at 100° C. for 168 hours
TER 113° C. = Tensile elongation retention (%), specimen aged at 113° C. for 168 hours
TER 136° C. = Tensile elongation retention (%), specimen aged at 136° C. for 168 hours
WR = Weight Retained, specimen aged at 100° C., 113° C., and 136° C. for 168 hours
Surface Exudate = inspected at 1, 3, and 7 days @ temperatures from 100 to 136° C.
VR = Volume Resistivity (ohms · cm)

As can be seen from the results in Table 4, Samples S1-S4 are sufficiently soft and flexible (even at a temperature as low as −20° C.), provide excellent properties before and after heat aging, and show no or only slight exudation after being subject to the loop-spew test or aging at elevated temperatures.

Example 4—PVC Plasticized with Combination 2-EH FDC/eSO

Prepare plasticized PVC samples according to the formulations provided in Table 5, below, using the procedure described in Example 2, above. In the following Samples, the plasticizer employed in Sample S5 contains a blend of 90 wt % 2-EH FDC and 10 wt % of epoxidized soybean oil ("eSO"), based on the total plasticizer weight. The plasticizer of Sample S6 is a blend of 70 wt % 2-EH FDC and 30 wt % eSO, based on the total plasticizer weight. The plasticizer of Samples S7 and S8 are blends of 50 wt % 2-EH FDC and 50 wt % eSO, based on the total plasticizer weight. The plasticizer of Sample S9 is a blend of 30 wt % 2-EH FDC and 70 wt % eSO, based on the total plasticizer weight. The plasticizer of Sample S10 is a blend of 10 wt % 2-EH FDC and 90 wt % eSO, based on the total plasticizer weight. A Comparative Sample CS6, which contains a 100 wt % eSO plasticizer, is also provided.

TABLE 5

S5-S10 and CS6 Sample Compositions

|  | S5 | S6 | S7 | S8 | S9 | S10 | CS6 |
|---|---|---|---|---|---|---|---|
| PVC (wt %) | 57.3 | 57.3 | 57.3 | 57.3 | 57.3 | 57.3 | 57.3 |
| Filler (wt %) | 6.4 | 6.4 | 6.4 | 6.4 | 6.4 | 6.4 | 6.4 |
| Heat Stabilizer (wt %) | 3.0 | 3.0 | 3.0 | 3.0 | 3.0 | 3.0 | 3.0 |
| Flame Retardant (wt %) | 3.0 | 3.0 | 3.0 | 3.0 | 3.0 | 3.0 | 3.0 |
| Antioxidant (wt %) | 0.3 | 0.3 | 0.3 | 0.3 | 0.3 | 0.3 | 0.3 |
| 90:10 2-EH FDC:eSO (wt %) | 30.0 | — | — | — | — | — | — |
| 70:30 2-EH FDC:eSO (wt %) | — | 30.0 | — | — | — | — | — |
| 50:50 2-EH FDC:eSO (wt %) | — | — | 30.0 | 30.0 | — | — | — |
| 30:70 2-EH FDC:eSO (wt %) | — | — | — | — | 30.0 | — | — |
| 10:90 2-EH FDC:eSO (wt %) | — | — | — | — | — | 30.0 | — |
| eSO (wt %) | — | — | — | — | — | — | 30.0 |
| Total | 100 | 100 | 100 | 100 | 100 | 100 | 100 |
| Plasticizer phr | ~52 | ~52 | ~52 | ~52 | ~52 | ~52 | ~52 |

Analyze Samples S5-S10 and Comparative Sample CS6 according to the above-described procedures. The results are provided in Table 6, below.

TABLE 6

Properties of Samples S5-S10 and CS6

|  | S5 (90:10 2-EH FDC:eSO) | S6 (70:30 2-EH FDC:eSO) | S7 (50:50 2-EH FDC:eSO) | S8 (50:50 2-EH FDC:eSO) | S9 (30:70 2-EH FDC:eSO) | S10 (10:90 2-EH FDC:eSO) | CS6 (eSO) |
|---|---|---|---|---|---|---|---|
| Mixing Time after Plasticizer Absorption and Before Filler Addition (min) | 20 | 20 | 20 | 10 | 20 | 20 | 20 |
| Plasticizer absorption time (min) | 4.0 | 4.0 | 4.0 | 3.5 | 4.0 | 4.0 | 4.0 |
| Shore D Hardness | 25.6 ± 0.3 | 28.8 ± 0.6 | 30.5 ± 0.8 | 30.8 ± 4.9 | 30.5 ± 0.4 | 32.3 ± 0.4 | 32.6 ± 0.6 |
| Shore A Hardness | 81.9 ± 1.1 | 85.2 ± 0.9 | 86.7 ± 0.8 | 84.1 ± 0.6 | 87.1 ± 0.8 | 88.4 ± 0.5 | 88.0 ± 0.5 |
| TS, unaged (psi) | 2793 ± 39 | 3170 ± 144 | 3188 ± 70 | 2916 ± 141 | 3387 ± 235 | 3266 ± 177 | 3054 ± 321 |
| TSR after 100° C. aging (%) | 99 ± 5 | 96 ± 7 | 116 ± 2 | 115 ± 7 | 93 ± 8 | 107 ± 13 | 102 ± 14 |

TABLE 6-continued

Properties of Samples S5-S10 and CS6

|  | S5 (90:10 2-EH FDC:eSO) | S6 (70:30 2-EH FDC:eSO) | S7 (50:50 2-EH FDC:eSO) | S8 (50:50 2-EH FDC:eSO) | S9 (30:70 2-EH FDC:eSO) | S10 (10:90 2-EH FDC:eSO) | CS6 (eSO) |
|---|---|---|---|---|---|---|---|
| TSR after 113° C. aging (%) | 187 ± 4 | 136 ± 9 | 98 ± 11 | 127 ± 12 | 84 ± 7 | 98 ± 8 | 91 ± 8 |
| TSR after 136° C. aging (%) | 232 ± 9 | 145 ± 22 | 114 ± 6 | 139 ± 7 | 91 ± 3 | 94 ± 10 | 90 ± 16 |
| TE, unaged (%) | 303 ± 13 | 306 ± 24 | 308 ± 5 | 310 ± 17 | 320 ± 10 | 310 ± 22 | 296 ± 28 |
| TER after 100° C. aging (%) | 40 ± 5 | 72 ± 8 | 84 ± 3 | 89 ± 9 | 87 ± 8 | 101 ± 7 | 100 ± 12 |
| TER after 113° C. aging (%) | 1 ± 1 | 7 ± 10 | 60 ± 21 | 82 ± 11 | 90 ± 7 | 96 ± 10 | 102 ± 9 |
| TER after 136° C. aging (%) | 1 ± 1 | 0 ± 0 | 54 ± 20 | 45 ± 14 | 79 ± 5 | 90 ± 9 | 88 ± 8 |
| WR after 7 days at 100° C. aging (%) | 89.0 | 89.9 | 93.9 | 91.7 | 95.6 | 98.4 | 100.1 |
| WR after 7 days at 113° C. aging (%) | 75.8 | 80.9 | 86.5 | 87.0 | 91.1 | 97.0 | 100.0 |
| WR after 7 days at 136° C. aging (%) | 71.3 | 78.3 | 85.0 | 84.3 | 90.7 | 96.2 | 99.4 |
| E' at −20° C. (MPa) | — | — | — | 3.00E+03 | — | — | — |
| Surface Exudate | None | None at 100 & 113° C.; Slight at 136° C. | None at 100 & 113° C.; Moderate at 136° C. | None | None | None | None |
| Loop spew, 48 hrs at 23° C. | None | None | None | None | None | Slight | Slight |
| VR at 23° C. (Ohms·cm) | — | — | — | 1.41E+15 | — | — | — |

TS = Tensile strength, ASTM D638
TSR = Tensile strength retention, ASTM D638
TSR 100° C. = Tensile strength retention, (%), specimen aged at 100° C. for 168 hours
TSR 113° C. = Tensile strength retention, (%), specimen aged at 113° C. for 168 hours
TSR 136° C. = Tensile strength retention, (%), specimen aged at 136° C. for 168 hours
TE = Tensile elongation, ASTM D638
TER = Tensile elongation retention, ASTM D638
TER 100° C. = Tensile elongation retention (%), specimen aged at 100° C. for 168 hours
TER 113° C. = Tensile elongation retention (%), specimen aged at 113° C. for 168 hours
TER 136° C. = Tensile elongation retention (%), specimen aged at 136° C. for 168 hours
WR = Weight Retained, specimen aged at 100° C., 113° C., and 136° C. for 168 hours
Surface Exudate=inspected at 1, 3, and 7 days@temperatures from 100 to 136° C. VR=Volume Resistivity (ohms·cm)

The results provided in Table 6 show that Samples S5-S10 are sufficiently soft and flexible (even at a temperature as low as −20° C.), provide acceptable properties before and after heat aging, and show no, only slight, or only moderate exudation after being subject to the loop-spew test or aging at elevated temperatures, even in combinations of bis(2-ethylhexyl) 2,5-furandicarboxylate with eSO over a broad range of concentration combinations. It is noted that the heat-aged performance improves with increasing concentration of eSO; regardless, even 10 wt % of eSO in the plasticizer shows significant improvement over bis(2-ethylhexyl) 2,5-furandicarboxylate alone (compare with CS4 and CS5, above).

Example 5—PVC Plasticized with Combination 2-EH/C8/C10 FDC/eSO

Prepare plasticized PVC samples according to the formulations provided in Table 7, below, using the procedure described in Example 2, above. In the following Samples, the plasticizer employed in Sample S11 contains a blend of 90 wt % 2-EH/C8/C10 FDC and 10 wt % eSO, based on the total plasticizer weight. The plasticizer of Sample S12 is a blend of 50 wt % 2-EH/C8/C10 FDC and 50 wt % eSO, based on the total plasticizer weight. The plasticizer of Sample S13 is a blend of 10 wt % 2-EH/C8/C10 FDC and 90 wt % eSO, based on the total plasticizer weight. For comparison, Comparative Sample CS6 is also reproduced in Tables 7 and 8, below.

TABLE 7

S11-S13 and CS6 Sample Compositions

|  | S11 | S12 | S13 | CS6 |
|---|---|---|---|---|
| PVC (wt %) | 57.3 | 57.3 | 57.3 | 57.3 |
| Filler (wt %) | 6.4 | 6.4 | 6.4 | 6.4 |
| Heat Stabilizer (wt %) | 3.0 | 3.0 | 3.0 | 3.0 |
| Flame Retardant (wt %) | 3.0 | 3.0 | 3.0 | 3.0 |
| Antioxidant (wt %) | 0.3 | 0.3 | 0.3 | 0.3 |
| 90:10 2-EH/C8/C10 FDC:eSO (wt %) | 30.0 | — | — | — |
| 50:50 2-EH/C8/C10 FDC:eSO (wt %) | — | 30.0 | — | — |
| 10:90 2-EH/C8/C10 FDC:eSO (wt %) | — | — | 30.0 | — |
| eSO (wt %) | — | — | — | 30.0 |
| Total | 100 | 100 | 100 | 100 |
| Plasticizer phr | ~52 | ~52 | ~52 | ~52 |

Analyze Samples S11-S13 according to the above-described procedures. The results are provided in Table 8, below.

TABLE 8

Properties of Samples S11-S13 and CS6

|  | S11 (90:10 2-EH/C8/C10 FDC:eSO) | S12 (50:50 2-EH/C8/C10 FDC:eSO) | S13 (10:90 2-EH/C8/C10 FDC:eSO) | CS6 (eSO) |
| --- | --- | --- | --- | --- |
| Mixing Time after Plasticizer Absorption and Before Filler Addition (min) | 20 | 10 | 20 | 20 |
| Plasticizer absorption time (min) | 4.0 | 5.0 | 4.0 | 4.0 |
| Shore D Hardness | 28.6 ± 0.6 | 30.4 ± 0.4 | 32.2 ± 0.4 | 32.6 ± 0.6 |
| Shore A Hardness | 85.8 ± 0.7 | 85.6 ± 1.0 | 88.0 ± 1.0 | 88.0 ± 0.5 |
| TS, unaged (psi) | 2961 ± 78 | 3130 ± 85 | 3455 ± 59 | 3054 ± 321 |
| TSR after 100° C. aging (%) | 99 ± 6 | 97 ± 13 | 97 ± 7 | 102 ± 14 |
| TSR after 113° C. aging (%) | 91 ± 8 | 111 ± 9 | 79 ± 5 | 91 ± 8 |
| TSR after 136° C. aging (%) | 177 ± 10 | 128 ± 6 | 86 ± 4 | 90 ± 16 |
| TE, unaged (%) | 308 ± 13 | 308 ± 11 | 318 ± 7 | 296 ± 28 |
| TER after 100° C. aging (%) | 98 ± 10 | 88 ± 20 | 101 ± 4 | 100 ± 12 |
| TER after 113° C. aging (%) | 82 ± 11 | 92 ± 9 | 88 ± 8 | 102 ± 9 |
| TER after 136° C. aging (%) | 1 ± 0 | 73 ± 5 | 87 ± 6 | 88 ± 8 |
| WR after 7 days at 100° C. aging (%) | 96.8 | 96.7 | 99.5 | 100.1 |
| WR after 7 days at 113° C. aging (%) | 89.9 | 93.4 | 98.7 | 100.0 |
| WR after 7 days at 136° C. aging (%) | 75.6 | 87.0 | 96.9 | 99.4 |
| E' at −20° C. (MPa) | — | 2.85E+03 | — | — |
| Surface Exudate | None | None | None | None |
| Loop spew, 48 hrs at 23° C. | Slight | None | Slight | Slight |
| VR at 23° C. (Ohms cm) | — | 1.74E+15 | — | — |

TS = Tensile strength, ASTM D638
TSR = Tensile strength retention, ASTM D638
TSR 100° C. = Tensile strength retention, (%), specimen aged at 100° C. for 168 hours
TSR 113° C. = Tensile strength retention, (%), specimen aged at 113° C. for 168 hours
TSR 136° C. = Tensile strength retention, (%), specimen aged at 136° C. for 168 hours
TE = Tensile elongation, ASTM D638
TER = Tensile elongation retention, ASTM D638
TER 100° C. = Tensile elongation retention (%), specimen aged at 100° C. for 168 hours
TER 113° C. = Tensile elongation retention (%), specimen aged at 113° C. for 168 hours
TER 136° C. = Tensile elongation retention (%), specimen aged at 136° C. for 168 hours
WR = Weight Retained, specimen aged at 100° C., 113° C., and 136° C. for 168 hours
Surface Exudate = inspected at 1, 3, and 7 days @ temperatures from 100 to 136° C.
VR = Volume Resistivity (ohms · cm)

The results provided in Table 8 show that Samples S11-S13 are sufficiently soft and flexible (even at a temperature as low as −20° C.), provide excellent properties before and after heat aging, and show no or only slight exudation after being subject to the loop-spew test or aging at elevated temperatures, even in combinations of 2-EH/C8/C10 FDC with eSO over a broad range of concentration combinations. It is noted that the heat-aged performance, particularly at a temperature of 136° C., improves with increasing concentration of eSO; regardless, even 10 wt % of eSO in the plasticizer shows significant improvement over 2-EH/C8/C10 FDC alone (compare with S1 and S2, above).

Example 6—PVC Plasticized with Combination DITD FDC/eSO

Prepare plasticized PVC samples according to the formulations provided in Table 9, below, using the procedure described in Example 2, above. In the following Samples, the plasticizer employed in Sample S14 contains a blend of 90 wt % DITD FDC and 10 wt % eSO, based on the total plasticizer weight. The plasticizer of Sample S15 is a blend of 50 wt % DITD FDC and 50 wt % eSO, based on the total plasticizer weight. The plasticizer of Sample S16 is a blend of 10 wt % DITD FDC and 90 wt % eSO, based on the total plasticizer weight. For comparison, Comparative Sample CS6 is also reproduced in Tables 9 and 10, below.

TABLE 9

S14-S16 and CS6 Sample Compositions

|  | S14 | S15 | S16 | CS6 |
| --- | --- | --- | --- | --- |
| PVC (wt %) | 57.3 | 57.3 | 57.3 | 57.3 |
| Filler (wt %) | 6.4 | 6.4 | 6.4 | 6.4 |
| Heat Stabilizer (wt %) | 3.0 | 3.0 | 3.0 | 3.0 |
| Flame Retardant (wt %) | 3.0 | 3.0 | 3.0 | 3.0 |
| Antioxidant (wt %) | 0.3 | 0.3 | 0.3 | 0.3 |
| 90:10 DITD FDC:eSO (wt %) | 30.0 | — | — | — |
| 50:50 DITD FDC:eSO (wt %) | — | 30.0 | — | — |
| 10:90 DITD FDC:eSO (wt %) | — | — | 30.0 | — |
| eSO (wt %) | — | — | — | 30.0 |
| Total | 100 | 100 | 100 | 100 |
| Plasticizer phr | ~52 | ~52 | ~52 | ~52 |

Analyze Samples S14-S16 according to the above-described procedures. The results are provided in Table 10, below.

TABLE 10

Properties of Samples S14-S16 and CS6

|  | S14 (90:10 DITD FDC:eSO) | S15 (50:50 DITD FDC:eSO) | S16 (10:90 DITD FDC:eSO) | CS6 (eSO) |
|---|---|---|---|---|
| Mixing Time after Plasticizer Absorption and Before Filler Addition (min) | 20 | 10 | 20 | 20 |
| Plasticizer absorption time (min) | 15.0 | 8.0 | 7.0 | 4.0 |
| Shore D Hardness | 34.0 ± 0.3 | 36.3 ± 0.9 | 33.6 ± 0.5 | 32.6 ± 0.6 |
| Shore A Hardness | 88.6 ± 1.1 | 90.0 ± 0.8 | 89.7 ± 1.3 | 88.0 ± 0.5 |
| TS, unaged (psi) | 3531 ± 141 | 3427 ± 46 | 3401 ± 84 | 3054 ± 321 |
| TSR after 100° C. aging (%) | 92 ± 5 | 94 ± 3 | 87 ± 4 | 102 ± 14 |
| TSR after 113° C. aging (%) | 86 ± 2 | 91 ± 6 | 82 ± 7 | 91 ± 8 |
| TSR after 136° C. aging (%) | 80 ± 3 | 94 ± 7 | 82 ± 10 | 90 ± 16 |
| TE, unaged (%) | 306 ± 4 | 325 ± 5 | 286 ± 10 | 296 ± 28 |
| TER after 100° C. aging (%) | 102 ± 7 | 92 ± 2 | 107 ± 7 | 100 ± 12 |
| TER after 113° C. aging (%) | 105 ± 11 | 92 ± 8 | 112 ± 4 | 102 ± 9 |
| TER after 136° C. aging (%) | 92 ± 3 | 73 ± 12 | 87 ± 6 | 88 ± 8 |
| WR after 7 days at 100° C. aging (%) | 100.1 | 100.3 | 100.1 | 100.1 |
| WR after 7 days at 113° C. aging (%) | 100.0 | 99.8 | 100.0 | 100.0 |
| WR after 7 days at 136° C. aging (%) | 99.5 | 95.9 | 99.3 | 99.4 |
| E' at −20° C. (MPa) | — | 2.83E+03 | — | — |
| Surface Exudate | None | None | None | None |
| Loop spew, 48 hrs at 23° C. | Slight | None | Slight | Slight |
| VR at 23° C. (Ohms cm) | — | 1.95E+15 | — | — |

TS = Tensile strength, ASTM D638
TSR = Tensile strength retention, ASTM D638
TSR 100° C. = Tensile strength retention, (%), specimen aged at 100° C. for 168 hours
TSR 113° C. = Tensile strength retention, (%), specimen aged at 113° C. for 168 hours
TSR 136° C. = Tensile strength retention, (%), specimen aged at 136° C. for 168 hours
TE = Tensile elongation, ASTM D638
TER = Tensile elongation retention, ASTM D638
TER 100° C. = Tensile elongation retention (%), specimen aged at 100° C. for 168 hours
TER 113° C. = Tensile elongation retention (%), specimen aged at 113° C. for 168 hours
TER 136° C. = Tensile elongation retention (%), specimen aged at 136° C. for 168 hours
WR = Weight Retained, specimen aged at 100° C., 113° C., and 136° C. for 168 hours
Surface Exudate = inspected at 1, 3, and 7 days @ temperatures from 100 to 136° C.
VR = Volume Resistivity (ohms · cm)

The results provided in Table 10 show that Samples S14-S16 are sufficiently soft and flexible (even at a temperature as low as −20° C.), provide excellent properties before and after heat aging, and show no or only slight exudation after being subject to the loop-spew test or aging at elevated temperatures, even in combinations of DITD FDC with eSO over a broad range of concentration combinations. It is noted that the heat-aged performance is very good with all mixture compositions of DITD FDC and eSO, just as with DITD FDC alone (compare with S3 and S4, above).

Example 7—PVC Plasticized with Combination DITD FDC/eFAME

Prepare plasticized PVC samples according to the formulations provided in Table 11, below, using the procedure described in Example 2, above. In the following Samples, the plasticizer employed in Sample S17 contains a blend of 50 wt % DITD FDC and 50 wt % of epoxidized fatty acid methyl ester ("eFAME"), based on the total plasticizer weight. The plasticizer of Sample S18 is a blend of 70 wt % DITD FDC and 30 wt % eFAME, based on the total plasticizer weight. A Comparative Sample CS7, which contains a 100 wt % eFAME plasticizer, is also provided.

TABLE 11

S17, S18, and CS7 Sample Compositions

|  | S17 | S18 | CS7 |
|---|---|---|---|
| PVC (wt %) | 57.3 | 57.3 | 57.3 |
| Filler (wt %) | 6.4 | 6.4 | 6.4 |
| Heat Stabilizer (wt %) | 3.0 | 3.0 | 3.0 |
| Flame Retardant (wt %) | 3.0 | 3.0 | 3.0 |
| Antioxidant (wt %) | 0.3 | 0.3 | 0.3 |
| 50:50 DITD FDC:eFAME (wt %) | 30.0 | — | — |
| 70:30 DITD FDC:eFAME (wt %) | — | 30.0 | — |
| eFAME (wt %) | — | — | 30.0 |
| Total | 100 | 100 | 100 |
| Plasticizer phr | ~52 | ~52 | ~52 |

Analyze Samples S17, S18, and CS7 according to the above-described procedures. The results are provided in Table 12, below.

TABLE 12

Properties of Samples S17, S18, and CS7

|  | S17 (50:50 DITD FDC:eFAME) | S18 (70:30 DITD FDC:eFAME) | CS7 (eFAME) |
|---|---|---|---|
| Mixing Time after Plasticizer Absorption and Before Filler Addition (min) | 20 | 20 | 20 |
| Plasticizer absorption time (min) | 8.0 | 10.0 | 4.0 |
| Shore D Hardness | 26.3 ± 0.2 | 29.6 ± 0.3 | 22.0 ± 0.3 |
| Shore A Hardness | 82.8 ± 1.0 | 85.5 ± 0.9 | 77.9 ± 0.9 |
| TS, unaged (psi) | 2844 ± 435 | 2993 ± 104 | 2389 ± 103 |
| TSR after 100° C. aging (%) | 121 ± 28 | 114 ± 4 | 141 ± 9 |
| TSR after 113° C. aging (%) | 119 ± 27 | 93 ± 5 | 203 ± 16 |
| TSR after 136° C. aging (%) | 115 ± 25 | 98 ± 2 | 234 ± 4 |
| TE, unaged (%) | 308 ± 52 | 310 ± 10 | 354 ± 16 |
| TER after 100° C. aging (%) | 87 ± 21 | 94 ± 3 | 61 ± 8 |
| TER after 113° C. aging (%) | 81 ± 21 | 93 ± 1 | 1 ± 0 |
| TER after 136° C. aging (%) | 76 ± 19 | 79 ± 7 | 1 ± 0 |
| WR after 7 days at 100° C. aging (%) | 92.4 | 95.2 | 84.4 |
| WR after 7 days at 113° C. aging (%) | 89.4 | 93.5 | 77.2 |
| WR after 7 days at 136° C. aging (%) | 87.4 | 92.2 | 71.1 |
| Surface Exudate | None | None | None |
| Loop spew, 48 hrs at 23° C. | Slight | Slight | Slight |

TS = Tensile strength, ASTM D638
TSR = Tensile strength retention, ASTM D638
TSR 100° C. = Tensile strength retention, (%), specimen aged at 100° C. for 168 hours
TSR 113° C. = Tensile strength retention, (%), specimen aged at 113° C. for 168 hours
TSR 136° C. = Tensile strength retention, (%), specimen aged at 136° C. for 168 hours
TE = Tensile elongation, ASTM D638
TER = Tensile elongation retention, ASTM D638
TER 100° C. = Tensile elongation retention (%), specimen aged at 100° C. for 168 hours
TER 113° C. = Tensile elongation retention (%), specimen aged at 113° C. for 168 hours
TER 136° C. = Tensile elongation retention (%), specimen aged at 136° C. for 168 hours
WR = Weight Retained, specimen aged at 100° C., 113° C., and 136° C. for 168 hours
Surface Exudate = inspected at 1, 3, and 7 days @ temperatures from 100 to 136° C.

The results provided in Table 12 show that Samples S17 and S18 are sufficiently soft and flexible, provide excellent properties before and after heat aging, and show no or only slight exudation after being subject to the loop-spew test or aging at elevated temperatures, even in combinations of DITD with eFAME over a range of concentration combinations. In particular, the combination DITD FDC:eFAME plasticizers showed marked improvement in tensile elongation following heat aging compared to eFAME used as the sole plasticizer.

The invention claimed is:

1. A plasticized polymeric composition, comprising:
   a polymer; and
   a plasticizer comprising a mixture of dialkyl 2,5-furandicarboxylates having the structure:

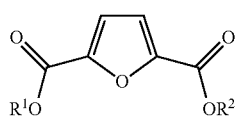

wherein $R^1$ and $R^2$ are independently selected alkyl groups,
   wherein $R^1$ is selected from the group consisting of a 2-ethylhexyl group, an octyl group, and a nonyl group;
   $R^2$ is a $C_{10}$-$C_{13}$ alkyl group; and
   wherein said plasticizer is a liquid at 22° C. and 1 atmosphere of pressure and the $R^1$:$R^2$ mole % ratio is from 30:70 to 70:30.

2. The composition of claim 1, wherein $R^2$ is selected from iso-branched $C_{10}$ to $C_{13}$ alkyl groups.

3. The composition of claim 1, wherein is a 2-ethylhexyl group.

4. The composition of claim 1, wherein is a 2-ethylhexyl group and an octyl group; and
   and $R^2$ is a decyl group.

5. The composition of claim 1, wherein said polymer is a vinyl chloride resin.

6. The composition of claim 5, wherein said vinyl chloride resin is polyvinyl chloride.

7. The composition of claim 1, wherein said plasticized polymeric composition has a tensile elongation retention of at least 30% when aged at 113° C. for 168 hours, as determined by ASTM D638.

8. A coated conductor comprising a conductive core and a polymeric layer surrounding at least a portion of said conductive core, wherein said plasticized polymeric composition of claim 1 constitutes said polymeric layer.

9. The composition of claim 1, wherein is an 2-ethylhexyl group; and
   $R^2$ is a dodecyl group.

10. The composition of claim 1, wherein the composition comprises:
    from 50 wt % to 65 wt % of the polymer; and
    from 25 wt % to 35 wt % of the plasticizer, based on the entire weight of the composition.

11. The composition of claim 1, wherein the plasticizer further comprises an epoxidized natural oil.

12. The composition of claim 1, wherein the plasticizer further comprises an epoxidized fatty acid alkyl ester.

13. The composition of claim 1, wherein $R^2$ is selected from the group consisting of a decyl group, a dodecyl group, an isotridecyl group, and a tridecyl group.

* * * * *